United States Patent [19]

Boczán

[11] Patent Number: 5,664,578
[45] Date of Patent: Sep. 9, 1997

[54] METHOD AND INSTRUMENT FOR SENSING FATIGUE, SHOCK AND/OR ACUTE STRESS

[76] Inventor: János Boczán, Dévai utca 22-26/b, H-1134 Budapest, Hungary

[21] Appl. No.: 397,275

[22] PCT Filed: Jan. 22, 1993

[86] PCT No.: PCT/HU93/00003

§ 371 Date: Mar. 10, 1995

§ 102(e) Date: Mar. 10, 1995

[87] PCT Pub. No.: WO94/05206

PCT Pub. Date: Mar. 17, 1994

[30] Foreign Application Priority Data

Sep. 9, 1992 [HU] Hungary ............... 1812/88

[51] Int. Cl.⁶ ............................................. A61B 5/00
[52] U.S. Cl. ............................................. 128/736
[58] Field of Search ........................... 128/664, 736

[56] References Cited

U.S. PATENT DOCUMENTS 5,247,940  9/1993  Wilk ............................... 128/736
5,366,483  11/1994 Sadkhin ........................ 128/736 X
5,385,529  1/1995  Koch ............................ 128/736 X

FOREIGN PATENT DOCUMENTS 29 01 865  7/1979  Germany.

Primary Examiner—Angela D. Sykes
Assistant Examiner—Ryan Carter
Attorney, Agent, or Firm—Spencer & Frank

[57] ABSTRACT

An instrument for sensing fatigue, includes a first temperature sensor for measuring a first temperature at a hottest spot of an uncovered part of a person's body; a second temperature sensor for measuring a second temperature at a coldest spot of an uncovered part of a person's body; and a comparator connected to the first and second temperature sensors for generating a temperature signal representing a temperature difference between the first and second temperatures.

16 Claims, 1 Drawing Sheet

5,664,578

METHOD AND INSTRUMENT FOR SENSING FATIGUE, SHOCK AND/OR ACUTE STRESS

FIELD OF THE INVENTION

The subject of the invention is a method for controlling the progress of fatigue of a person doing some kind of a tiring activity and for the prevention of the effects of fatigue. Subject of the invention is further an instrument for sensing fatigue, states of shock and/or acute stress, completed with a device for evaluating the temperatures on the surface of parts of the body.

An activity most typically tiring, the breaking off of which usually depends not on the state of fatigue but on other factors (e.g. arriving at the destination, end of shift, etc.), is driving a car.

It is known that most people become alert and active when starting driving, which, among other things, manifests itself in an increased stimulus of motion and speech. After several hours of driving, drivers grow more irritable, their movements get slower and their way of driving becomes more careless. It is provable that pending on the distance and the time of driving, a temporary vascular stenosis appears, mainly in the small blood vessels of the drivers. People in this state more often have accidents, that is why it is important to recognize and prevent or cancel this condition. It is also known that the states of shock and acute stress primarily appear in the form of the constriction of the small vessels.

DESCRIPTION OF THE PRIOR ART

There exists a diagnostic method (Hungarian patent of the Inventor No. 191 121) capable of examining people (expediently drivers) exposed to stress, which is based on the statistical processing of the changes in thermograms of the face, and the purpose of which is to detect and measure the tolerance of drivers and the damages coming from their occupation. According to the procedure, thermograms—pictures of the infrared radiation—of the face and hands of the person to examine are made before the stress is to appear. The differences in the various parts of the thermograms are recorded in a quantitative way, on the basis of the dominant isotherms, The patients can be examined again after the stress influence, depending on the aim of the examination.

There is not known any applicable method based on the above principle to detect the process of fatigue, because it is too complicated and time-taking.

There is a treatment for fatigue by means of an instrument (EP 0 209 246 A1) generating electromagnetic fields mounted on the back of the driver's seat. It consists of the flat coil on the back of the seat and an impulse generator connected to it. The impulse generator produces 5 impulses 5 msec long each with 15 msec long pauses, repeating this for 30 minutes with 100 msec pauses every four hours.

The flux density induced in the coil is 50 Gauss of which a flux density of 15 Gauss falls on the body surface. According to the description, the instrument is good for the relaxation of the drivers muscles.

Whereas this instrument is suitable for relieving the fatigue of drivers, the way of application outlined in the description, the length and repetition of the treatment do not agree with the regeneration needs of the driver as the exposure is less frequent and much longer than it would be the best for him.

SUMMARY OF THE INVENTION

Aim of the invention is to develop a method and instrument to control fatigue, making it possible to perform the treatment in the course of the fatiguing activity at the optimum time, and depending on the degree of fatigue.

Basis of the invention is the recognition that the drop of the temperature of the acrons—i.e. the free surfaces of the human body woven through with small blood vessels—, compared to the inner temperature of the body is characteristic of the state of fatigue. Furthermore it is satisfactory to watch the temperature fluctuation of one such surface point to draw conslusions. It is serviceable to choose the auricle as a surface point.

The solution of the task according to the invention is a procedure to control the process of fatigue of a person displaying a tiring activity, and the prevention of the effects of fatigue. First, the temperatures of the to estimated coldest and hottest spots on the head of the person still in a state of rest are taken. Then, in the course of his activity, temperature measurement is carried out from time to time or continuously, on the same—either the coldest or the hottest and the coldest—spots of the head. Then the difference of the related temperature data of the hottest and the coldest spots are taken, and the changes in the temperature differences are watched. When the change of the temperature difference exceeds a certain value, the person is warned of his state of fatigue and/or a fatigue-reducing treatment is administered.

It is advantageous to take the temperature of the inner canthus as the hottest spot on the head.

It is to the purpose to take the temperature of the upper part of the auricle as the coldest spot on the head.

It is advantageous to handle the temperature of the hottest spot on the head as an experimentally defined average or once-measured constant value.

It is to the purpose to apply a treatment of pulsing electro-magnetic field for reducing fatigue.

It is advantageous to administer the pulsing electro-magnetic treatment during the tiring activity.

It is to the purpose to go on with measuring the temperature during the fatigue-reducing treatment or refreshing of the driver and to stop the treatment when the difference of temperature reaches or approximates the value of the state of rest.

An instrument detecting fatigue, states of shock and/or acute stress is also a part of the invention, with a device evaluating temperatures on the surface of the parts of the body. That device has a memory for the constant values of the temperatures taken at the approx. hottest free (uncovered) spots on the surface of the parts of the body; or a temperature sensing capacity for measuring temperature data; also a temperature sensing capacity for measuring the temperature data of the relatively coldest spot of uncovered parts of the body, which are connected to the input of the device defining the temperature differences.

It is advantageous to fix the temperature sensor taking the temperature of the relatively coldest spot on the temple or the bridge of spectacles.

It is to the purpose to fix the temperature sensor taking the temperature of the inner canthus, too, on the spectacle-frame.

It is advantageous if the fatigue-sensing instrument has a limit value memory and a comparator.

It is to the purpose if the fatigue-sensing instrument has a sound-signal unit.

It is advantageous if the fatigue-sensing instrument is connected to a seat for pulsing electro-magnetic field treatment.

The advantage of the solution according the invention is that it makes possible the regular or continuous evaluation of the degree of fatigue of the person, without stopping his activity; the intervention at the optimum time; and the measuring of the effect of the fatigue-reducing treatment. The fatigue-sensing instrument is capable of accomplishing the method according to the invention; can be easily fixed on the examined person; does not disturb work; makes it possible to measure the degree of fatigue without disturbing work; and gives warnings to the person growing more tired.

The invention is also suitable for detecting and cancelling conditions that go together with the stenosis of the small vessels, the so called end arterioles.

Conditions like this are e.g. heavy stress influences and states of shock. This phenomenon first appears at the apices of the human organism, the so called acrons, thus at the tip of the nose and in the auricle.

The effect of the consumption of a small quantity of alcohol, in the beginning, is the dilatation of the blood vessels in question. The state brought about by the influence of alcohol is divided to different stages. Driving is highly worsened in the state when the stage of vasodilatation is followed by the vascular stenosis in the skin. These are the second and third stages. The flushed face gets pale. This condition again starts with the narrowing of the blood vessels in the nose and the external ear. Because of the vasoconstriction, these areas suddenly cool down.

DESCRIPTION OF THE PREFERRED EMBODIMENTS

Figure 1:
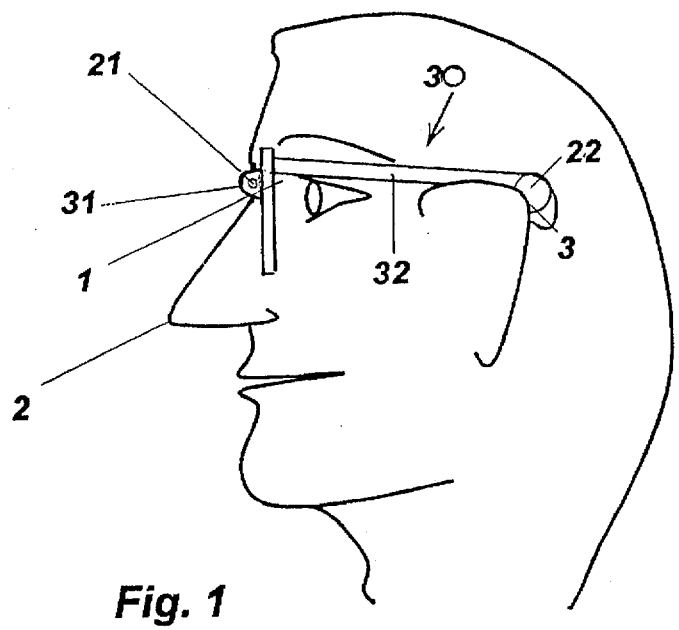
Figure 2:
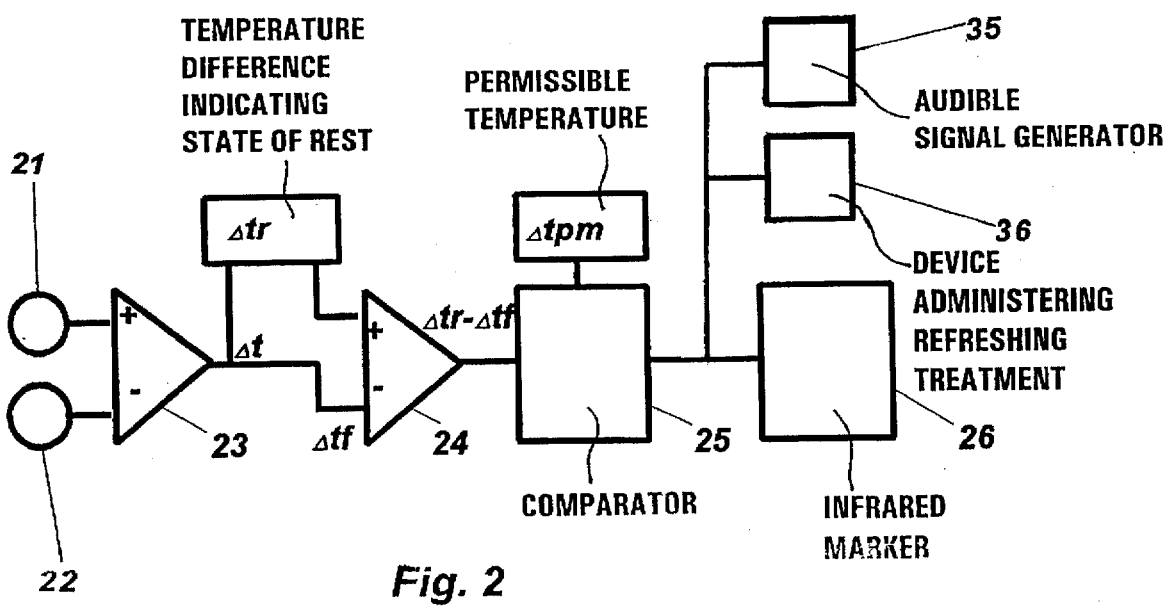

Hereinafter the invention is going to be outlined relying on an example of effectuation.

The method according to the invention is carried out on a bus driver.

In the course of the procedure, the face of the bus driver is examined periodically or continuously and the signs of fatigue caused by driving are evaluated. In the evaluation, the temperature of the inner canthus is compared with the temperature of the coldest spot in the face (expediently the nose), and the changes of the temperature difference are processed. The sign of tiredness is that the temperature of the nose decreases, thus the temperature difference between the canthus and the nose grows.

On perception of the sign of tiredness—suitably in the case of a heavier fatigue, defined by the length of time since the perception—the driver is given a pulsing electro-magnetic field treatment.

The parameters of the pulsing electro-magnetic (magnetic) field are as follows:

| | |
|---|---|
| magnetic induction: | 8 mT |
| impulse repetition frequency: | 5 Hz |
| impulse space factor: | 25% |
| length of pulse groups: | 100 msec |
| interval between pulse groups: | 100 msec. |

It has to be noted that the influence of the pulsing electro-magnetic field can be different depending on the pulse frequency: slower impulses (e.g. 2 pulse/sec) quicken the metabolism, while faster ones. (e.g. 50 pulse/sec) reduce it. In such a way, therefore, the relaxation or tenseness of the muscles, the dilatation or constriction of the blood vessels can be achieved as well.

By the help of the treatment, in a few minutes, the driver's small blood vessels that are narrowed because of his tiredness will dilate, which improves his blood supply in the face, and as a result, the signs of fatigue disappear from the face, and the nose and other cold spots of the face warm up. Continuously measuring the temperature of the coldest spot in the face during the refreshing treatment, we shall get information on the loosening of fatigue and the treatment can be finished. 1–20 minutes of treatment will give the best results, as in a period as long as that all muscles get relaxed.

The procedure can be carried out en route or at a stop (e.g. at the terminal station of a city line), but it is essential to accomplish the reference examination when the driver is still in a state of rest.

The examination can be performed by means of a monitor, by comparing the images displaying the temperature differences on the monitor, or in the computer processing unit. The evaluation is simplified by the fact that it is not necessary to process all the temperature changes of the face but it is enough to compare the temperature differences measured at the states of rest and fatigue at the hottest and the coldest spots of the face.

Starting and stopping the pulsing electro-magnetic field treatment can be done manually but automatically as well, when it is independent from the driver's will.

The results of the evaluation are recorded. Taking the mean values of the recorded date, the optimum length of the treatment and distance—covering which it is reasonable to carry out the treatment for all drivers—can be defined.

An instrument sensing fatigue can be advantageously used for the detection of the temperature difference between the inner canthus and the coldest spot of the face (the acrons—the tip of the nose—the auricle, etc.), with an infrared sensor directed to the inner canthus or a contact thermometer fixed on the bridge of a pair of spectacles. There is a similar thermometer built in the spectacle frame. It is either on a complement above the tip of the nose or on the temples of the frame, directed to the upper edge of the auricle. There is also a data processing electronic circuit in the temples of the frame and an infrared marker in the bridge. This latter one is partly to inform the person wearing the spectacles about the critical degree of his fatigue and partly to cooperate with the infrared receiver unit on the dashboard, starting and stopping the electro-magnetic treatment, controlled by the temperature difference. The fatigue sensing instrument includes a memory or a temperature sensor for the constant temperature value of the relatively hottest spot on the uncovered part of the body; and a temperature sensor for the relatively coldest surface of the uncovered part of the body, that are all connected to the input of a differential device. The differential device is fitted with another differential device that compares the momentary temperature difference with the temperature difference characteristic of the state of rest. To its output a comparator is connected that compares the difference value with the permissible value. The infraredmarker is connected to the comparator output.

The advantage of the fatigue sensing spectacles over a video camera is that temperature sensing only takes place at two constant points, thus it becomes needless to select the useful measurement data from among a superfluous set of data. The instrument made for this procedure is much simpler, less expensive and does not take a lot of room in the driver's cabin.

The degree of fatigue that demands intervention can be displayed by a fatigue sensing ear thermometer too. It can be fixed on the ear or the temple of the spectacles. When the driver puts it on its temperature sensing contact unit touches the back side of the auricle. It also includes a memory that stores the permissible value proportional to the temperature of the inner canthus; a circuit that compares the temperature taken by the contact unit to the value in the permissible value memory; and a sound signal to sign that the actual temperature taken by the contact unit sank below the permissible value.

The fatigue sensing instrument in the example is built in a spectacle frame.

On the spectacle there are further temperature sensors for measuring the temperatures of the inner canthus and one of the coldest spots (the auricle or the tip of the nose) on the head. The latter one is either fixed on the temple of the spectacle frame and directed to the upper edge of the auricle or on the bridge of the frame and directed to the tip of the nose. The two temperature sensors are electronically connected to a differential device. At its output a sign is displayed corresponding to the difference of the temperatures taken by the two temperature sensors at the same time. The temperature difference is compared to the one belonging to the state of rest. When the difference between the two temperature differences exceeds a permitted value (e.g. 4 degrees centigrade), the examined person is warned or given a refreshing treatment.

In a simple version of the construction the fastening part is a hook that can be affixed to the ear. The memory for the permitted value is either connected to the thermometer measuring the temperature of the inner canthus or it is sotred in the memory as a constant value that is already known. It is suitable if the signal is a buzzing sound which sounds depending on the comparison of the momentary temperature differences to a permitted value.

It is practical if the permitted value in this case is 32 degrees centigrade. In practice the display remains true enough in the temperature range good for driving (15–50 degrees centigrade) even if the permitted value is taken as constant.

Displays in different temperature ranges make it possible to adapt the instrument, i.e. the display system for detecting states of preshock or stress conditions dangerous for the organism or conditions of unfitness for driving (because of the effect of alcohol). To cancel these conditions, the pulsing electro-magnetic treatment is only partly suitable. That is why it is only the signalling of a dangerous condition that is important concerning the invention.

I claim:

1. A method of monitoring fatigue of a person performing a tiring activity and of preventing effects of fatigue, comprising the following steps:
   (a) while the person is at rest prior to performing the activity, taking a first temperature at a hottest spot and a second temperature at a coldest spot of the person's head;
   (b) repeatedly taking said first and second temperatures during the activity;
   (c) calculating a temperature difference between said first and second temperatures;
   (d) monitoring a change of said temperature difference during the activity;
   (e) generating a signal when said temperature difference exceeds a predetermined value.

2. The method as defined in claim 1, wherein step (b) is performed intermittently.

3. The method as defined in claim 1, wherein step (b) is performed continuously.

4. The method as defined in claim 1, further comprising the step of triggering a warning by the signal generated in step (e).

5. The method as defined in claim 1, wherein steps (a) and (b) comprise the step of taking said second temperature at the upper edge of the auricle.

6. The method as defined in claim 1, wherein steps (a) and (b) comprise the step of taking said first temperature at the inner canthus.

7. The method as defined in claim 1, further comprising the step of triggering, by the signal generated in step (e), a refreshing treatment administered to the person.

8. The method as defined in claim 7, comprising the steps of performing steps (b), (c) and (d) during performance of said refreshing treatment on the person at rest and discontinuing said treatment when said temperature difference at least approximates the temperature difference between the temperatures obtained in step (a).

9. The method as defined in claim 7, wherein said refreshing treatment comprises the step of applying a pulsing electromagnetic field.

10. The method as defined in claim 9, wherein said step of applying a pulsing electromagnetic field is performed during said activity.

11. A method of monitoring fatigue of a person performing a tiring activity and of preventing effects of fatigue, comprising the following steps:
    (a) taking a first temperature at a hottest spot of the person's head;
    (b) while the person is at rest prior to performing the activity, taking a second temperature at a coldest spot of the person's head;
    (b) repeatedly taking said second temperature during the activity;
    (c) calculating a temperature difference between said first and second temperatures;
    (d) monitoring a change of said temperature difference during the activity;
    (e) generating a signal when said temperature difference exceeds a predetermined value.

12. The method as defined in claim 11, wherein step (a) comprises the step of repeatedly taking said first temperature and further comprising the step of calculating an average of the first temperatures.

13. The method as defined in claim 11, wherein step (a) comprises the step of taking said first temperature once.

14. An instrument for sensing fatigue, comprisising:
    (a) a memory containing data representing a first, constant temperature of a relatively hottest spot an uncovered part of a person's body;
    (b) a temperature sensor for measuring a second temperature at a relatively coldest spot of an uncovered part of a person's body; and
    (c) comparator means connected to said memory said temperature sensor for generating a temperature signal representing a temperature difference between said first and second temperatures.

15. A combination of an instrument for sensing fatigue with a spectacle frame; comprising
    (a) a temple part comprised in said spectacle frame;
    (b) a bridge part comprised in said spectacle frame;
    (c) a first temperature sensor for measuring a first temperature at a hottest spot of a person's head;

(d) a second temperature sensor for measuring a second temperature at a coldest spot of the person's head; said second temperature sensor being mounted on one of said parts of the spectacle frame; and (e) comparator means connected said first and second temperature sensors for generating a temperature signal representing a temperature difference between said first and second temperatures.

16. A combination of an instrument for sensing fatigue with a spectacle frame; comprising (a) a first temperature sensor for measuring a first temperature at a hottest spot of a person's head; said first temperature sensor being mounted on said spectacle frame for measuring the temperature of the inner canthus;

(b) a second temperature sensor for measuring a second temperature at a coldest spot of the person's head; and (c) comparator means connected to said first and second temperature sensors for generating a temperature signal representing a temperature difference between said first and second temperatures.

* * * * *